United States Patent [19]

Campbell, deceased et al.

[11] Patent Number: 5,325,020

[45] Date of Patent: *Jun. 28, 1994

[54] CIRCULAR WAVEGUIDE PLASMA MICROWAVE STERILIZER APPARATUS

[75] Inventors: Bryant A. Campbell, deceased, late of Los Gatos, Calif., by Louise A. Campbell, legal representative; Vincent Formanek, Hillside, Ill.

[73] Assignee: AbTox, Inc., Mundelein, Ill.

[*] Notice: The portion of the term of this patent subsequent to Feb. 2, 2010 has been disclaimed.

[21] Appl. No.: 961,408

[22] Filed: Oct. 15, 1992

Related U.S. Application Data

[63] Continuation-in-part of Ser. No. 589,511, Sep. 28, 1990, Pat. No. 5,184,046.

[51] Int. Cl.⁵ .................................................. H01J 7/24
[52] U.S. Cl. ........................... 315/111.21; 315/39.53; 315/39.51; 315/3.5; 422/21; 422/24; 313/231.31; 250/455.11
[58] Field of Search ............. 315/111.21, 39.53, 39.51, 315/3.5; 313/231.31; 250/455.11; 422/21, 24

[56] References Cited

U.S. PATENT DOCUMENTS

| | | |
|---|---|---|
| 3,383,163 | 5/1968 | Menashi . |
| 3,410,776 | 11/1968 | Bersin . |
| 3,428,548 | 2/1969 | Hollahan . |
| 3,704,096 | 11/1972 | Verses et al. . |
| 3,737,608 | 6/1973 | Nagao et al. ................. 422/21 X |
| 3,851,436 | 12/1974 | Fraser et al. ................. 422/22 X |
| 3,948,601 | 4/1976 | Fraser et al. ................. 422/23 X |
| 4,065,369 | 12/1977 | Ogawa et al. ................. 204/164 |
| 4,123,663 | 10/1978 | Horiike ........................... 250/531 |
| 4,138,306 | 2/1979 | Niwa ................................ 156/345 |
| 4,151,034 | 4/1979 | Yamamoto ..................... 156/345 |
| 4,160,690 | 7/1979 | Shibagaki ........................ 156/643 |
| 4,169,123 | 9/1979 | Moore et al. .................. 422/29 |
| 4,169,124 | 9/1979 | Forstrom et al. .............. 422/33 |
| 4,207,286 | 6/1980 | Boucher ........................... 422/21 |
| 4,230,663 | 10/1980 | Forstrom et al. .............. 422/33 |
| 4,289,728 | 9/1981 | Peel et al. ....................... 422/24 |
| 4,321,232 | 3/1982 | Bithell ............................. 422/23 |
| 4,348,357 | 9/1982 | Bithell ............................. 422/22 |
| 4,366,125 | 12/1982 | Kodera et al. ................. 422/293 |
| 4,437,567 | 3/1984 | Jeng ................................. 422/28 X |
| 4,640,782 | 2/1987 | Burleson ......................... 210/748 |
| 4,643,876 | 2/1987 | Jacobs et al. ................... 422/23 |
| 4,801,427 | 1/1989 | Jacob ................................ 422/23 |
| 4,818,488 | 4/1989 | Jacob ................................ 422/23 |
| 4,898,715 | 2/1990 | Jacob ................................ 422/186.29 |
| 4,917,586 | 4/1990 | Jacob ................................ 422/21 |
| 4,931,261 | 6/1990 | Jacob ................................ 422/292 |
| 4,943,417 | 6/1990 | Jacob ................................ 422/292 |
| 4,976,920 | 12/1990 | Jacob ................................ 422/23 |
| 5,184,046 | 2/1993 | Campbell ........................ 315/111.21 |

FOREIGN PATENT DOCUMENTS

| | | |
|---|---|---|
| 109352 | 5/1983 | European Pat. Off. . |
| 268396 | 5/1989 | Fed. Rep. of Germany . |
| 58103460 | 12/1981 | Japan . |
| 58-87825 | 5/1983 | Japan . |
| 58-162276 | 9/1983 | Japan . |
| 2214081 | 1/1989 | United Kingdom . |
| 2253144 | 1/1991 | United Kingdom . |

OTHER PUBLICATIONS

Fraser et al., "Plasma Sterilization Technology for Spacecraft Applications", *NASA-CR-146314 Final Report* (Boeing Co.), Sep., 1975.

Hollahan et al., "Analytical Applications of Electrodelessly Discharged Gases", *Chemical Instrumental, Journal of Chem. Education*, 43:A401–A416, May 1966.

(List continued on next page.)

*Primary Examiner*—Robert J. Pascal
*Assistant Examiner*—Haissa Philogene
*Attorney, Agent, or Firm*—Majestic, Parsons, Siebert & Hsue

[57] ABSTRACT

An apparatus for plasma sterilization includes a sterilization chamber and at least one microwave plasma generator for producing gas plasma products communicating therewith. The microwave plasma generator comprises a cylindrical metal waveguide and an axially concentric antenna extending into the waveguide. The plasma generator includes an inner plasma container made of a electromagnetic transparent material.

7 Claims, 4 Drawing Sheets

OTHER PUBLICATIONS

Hollahan et al., "Research with Electrodelessly Discharged Gases," *Chemical Instrument*, 43:A497–A512, Jun., 1966.

Hollahan et al., "Chem. Education Letters," *Journal of Chem. Education* 43:392–393, Jul., 1966.

Hollahan et al., "Techniques and Applications of Plasma Chemistry," v–vii, 229–253 (1974).

Ross Caputo et al., "Alternative Sterilization Technologies Come of Age," *Medical Device and Diagnostic Industry*, vol. 14, No. 12, pp. 41–42 (1992).

Rudder et al., "Remote Plasma-Enhanced Chemical-Vapor Deposition of Epitaxial Ge Films," *J. Appl. Phys.*, 60(1):3522 (1986).

Leaper et al., "Influence of Temperature on the Synergistic Sporicidal Effect of Peracetic Acid Plus Hydrogen Peroxide on Bacillus Subtilis" *SA22 (NCA 72-52)*, Food Microbiology, 1:199–203, 1984.

Leaper et al., "A Note on the Effect of Storage on the Chemical Resistance of Spores of Bacillusu Subtilis SA22 and Bacillus Subtilis Glogigii B17," *J. Applied Biology*, 64:183–186, 1988.

Leaper et al., "Synergistic Killing of Spores of Bacillus Subtilis by Peracetic Acid and Alcohol," *J. Food Technology*, 19:355–360, 1984.

Ross A. Caputo et al., "Validation Testing of a Gas Plasma Sterilization System", *Medical Device and Diagnostic Industry*, vol. 15, #1, pp. 132–138, 1993.

Leaper et al., "Comparison of the Resistance to Hydrogen Peroxide of Wet and Dry Spores of Bacillus Subtilis SA222," J. Food Technology, 19:695–702, 1984.

Ross A. Caputo et al., "AbTox Plazlyte TM plasma sterilization", Cold Sterilization Beyond 1985: A Look at Alternatives to Dec. 1988 EtO, *Journal of Health-Care Material Management*, vol. 10, No. 8, Sep., 1992.

S. R. Goode, et al., *A Review of Instrumentation Used to Generate Microwave-Induced Plasmas*, Applied Spectroscopy Feature Article, vol. 38, No. 6, 1984.

Peter A. Rizzi, *Microwave Engineering Passive Circuits*, Prentice Hall, Library of Congress Cataloging-in-Publication Data, (1988).

Victor F. Valey, Ph.D., *Modern Microwave Technology*, Prentice Hall, Library of Congress Cataloging-in-Publication Data, (1987).

Om P. Gandhi, *Microwave Engineering and Applications*, Pergamon Press, Library of Congress Cataloguing in Publication Data, (1988).

07321483 Mar. 1989 Campbell et al.

07475602 Feb. 1990 Campbell et al.

CIRCULAR WAVEGUIDE PLASMA MICROWAVE STERILIZER APPARATUS

RELATIONSHIP TO COPENDING APPLICATION

This application is a continuation-in-part of copending application Ser. No. 07/589,511 filed Sep. 28, 1990 U.S. Pat. No. 5,184,046.

FIELD OF INVENTION

This invention relates to an apparatus for sterilizing articles with a gas plasma generated from a gas mixture of oxidizing and/or reducing agents. In particular, this invention relates to a plasma sterilizing apparatus having a sterilizing chamber communicating with a plasma generator. The plasma generator is a cylindrical waveguide microwave plasma system including an antenna which injects the microwave energy field axially into a sealed coaxial gas containing an antechamber which is transparent to the microwave energy.

BACKGROUND OF THE INVENTION

A variety of gas sterilization methods has been investigated in the past. Methods using ethylene oxide and other disinfecting gases are widely used for sterilizing a wide range of medical products from pharmaceutical preparations to surgical instruments. Irradiation alone and together with disinfecting gases has also been investigated, as summarized by Russell, A.; *The Destruction of Bacterial Spores*; New York: Academic Press (1982).

A sterilizing method must effectively kill all organisms, including spores, without damage to the article or goods being sterilized. However, many disinfecting methods which meet this criteria, such as ethylene oxide and irradiation methods, have been found to expose workers and the environment to unacceptable safety hazards. States and Federal legislation are severely restricting the amount of hazardous gases such as ethylene oxide (a carcinogen) in the working environment, or the use of any system or method which produces toxic residues or exhaust products. This is presenting a major crisis in hospitals and other areas of the health industry.

The use of plasma to sterilize containers was suggested in U.S. Pat. No. 3,383,163. Plasma is an ionized body of gas which may be generated by the application of power from different sources. The ionized gas will contact microorganisms on the surfaces of the items to be sterilized and effectively destroy the microorganisms.

Sterilizing plasmas have been generated with a wide variety of gases: argon, helium or xenon (U.S. Pat. No. 3,851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or freon with pulsed pressure (U.S. Pat. No. 4,348,357); hydrogen peroxide (U.S. Pat. No. 4,643,876); nitrous oxide, alone or mixed with oxygen, helium or argon (Japanese Application Disclosure No. 103460-1983); and nitrous oxide, alone or mixed with ozone (Japanese Application No. 162276-1983). Unfortunately, these plasma methods have proven to be too corrosive to articles being sterilized, and particular packaging materials; have left toxic residues on the sterilized articles; or have presented other safety or environmental hazards.

Non-plasma gas sterilization procedures have been described using ozone (U.S. Pat. No. 3,704,096) and hydrogen peroxide (U.S. Pat. Nos. 4,169,123; 4,169,124; 4,230,663; 4,366,125; 4,289,728; 4,437,567; and 4,643,876). These materials are toxic and leave undesirable residues.

DESCRIPTION OF THE PRIOR ART

Plasma gas sterilizer systems described in U.S. Pat. Nos. 3,851,436 and 3,948,601 have a plasma RF generation chamber and a separate sterilizing chamber. Products of a gas plasma produced in the chamber with argon, helium, nitrogen, oxygen or xenon are passed into a separate sterilization vacuum chamber. U.S. Pat. No. 4,643,876 describes a hydrogen peroxide plasma RF generation chamber which also functions as the sterilizing chamber. The articles being sterilized are exposed directly to electromagnetic radiation, damaging nonmetallic components of the articles or packages being sterilized. Matching networks or equivalent adjusting means are required with RF systems to adjust the system to the conductivity variations in the electromagnetic field of the plasma generating zone introduced by metallic articles.

Goode, S. R. et al., *Appl. Spectroscopy*. 38:755–763 (1984), disclose a variety of microwave generating systems, including use of cylindrical cavity plasma systems with axial microwave generators. The TM operating modes and their advantages are also defined.

Rizzi, P. A., *Microwave Engineering Passive Circuits.*, New Jersey: Prentice-Hall, pp. 216–217 (1988), discloses a cylindrical waveguide in $TM_{01}$ mode.

Veley, V. F., *Modern Microwave Technology.* New Jersey: Prentice-Hall, pp 132–135 (1987), discloses a cylindrical waveguide in $TM_{01}$ mode.

SUMMARY AND OBJECTS OF THE INVENTION

The apparatus of this invention is an apparatus for plasma sterilization comprising a sterilization chamber and at least one microwave plasma generator for producing gas plasma products communicating therewith. The plasma generator comprises a cylindrical metal waveguide, and an antenna which injects the microwave energy field axially into a sealed coaxial gas containing an antechamber which is transparent to the microwave energy. One end of the waveguide is closed with a metal plate, and the antenna extends therethrough. The other end of the waveguide is closed with a metal plate having an outlet passageway for exit of plasma gas products, the outlet passageway and the waveguide having a common central axis. However, it is important to note, that according to the present invention, it is not necessary to have a common central axis, and plasma gas products can be brought out at any angle to the axis of the waveguide.

Preferably, the waveguide has an inner plasma container, preferably a concentric, cylindrical container, made of an electromagnetic transparent material such as quartz or TEFLON, the container having a gas inlet and a plasma product outlet conduit. It can have a distributor arrangement communicating with the plasma gas generator, for distributing plasma gas products in the sterilizing chamber. Optimally, the waveguide has an axial length L, corresponding to the formula:

$$L = (n)\lambda_g/2$$

wherein n is an integer, and $\lambda_g$ is the guide wavelength of the wave guide and is defined by the following:

$$\lambda_g = \frac{\lambda}{\sqrt{1 - \left(\frac{f_c}{f}\right)^2}}$$

where
$\lambda$ = wavelength
$f_c$ = cutoff frequency
$f$ = operating frequency of the electromagnetic field generator The diameter (D) of the wave guide is further defined by this relationship →$\lambda_c$ = 1.31 D, $\lambda_c$ corresponding to the cutoff wavelength.

A plasma is, by definition, a partially ionized gas containing molecules, atoms, ions, electrons and free radicals. At lower pressures, it has been determined that electron temperatures are typically many times greater than the temperatures of free radicals and of the gas itself. This nonequilibrium plasma system is defined as a cold plasma. The cold plasma is further defined as having a high E/P ratio, where E is the electric field strength and P is the pressure. Circular wave guides operating in the $TM_{01}$ mode generate electric field strengths which are greater in magnitude than the traditional rectangular waveguide methods of coupling microwave energy into a plasma antechamber, and therefore, is the preferred method of implementation for the generation of the maximum number of free radicals at the lowest possible temperature.

It is an object of this invention to provide a plasma sterilizer which operates at low temperatures, low gas consumption and effectively sterilizes all types of articles, packaged or unpackaged, without damaging the article or packaging.

It is a further object of this invention to provide a plasma sterilizer which provides sterilizing gaseous plasma products which can be used alone or in conjunction with ancillary treatment of articles with vaporized antimicrobial chemicals to provide complete killing of spores.

DETAILED DESCRIPTION OF THE PREFERRED EMBODIMENTS

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. Ethylene oxide is now known to be a dangerous carcinogen, however, and a number of new state laws protecting worker safety and the environment are precluding or greatly restricting further use of ethylene oxide sterilizers in hospital environments.

Numerous gas plasma sterilizers using a wide variety of gases have been described in the patent literature. A few have been commercially produced, and a few have focused on residue contamination problems. The previously described gas sterilizers either fail to satisfy current regulatory residue and exhaust emission safety standards of several states, because they either leave unacceptable residues or produce exhaust emissions which are potentially hazardous to hospital personnel, or they cause unacceptable destruction of packaging materials. They are thus not satisfactory for replacing ethylene oxide sterilizers.

The gas sterilizer of this invention produces a plasma from gas mixtures containing argon, helium and/or nitrogen; and oxygen and/or hydrogen; and optional inert gases. The exhaust gas products fully satisfy current environmental and worker safety concerns, the products of the plasma being almost entirely water vapor, carbon dioxide and non-toxic gases normally found in the atmosphere.

The term "plasma" as used herein is defined to include any portion of the gas or vapors which contain electrons, ions, free radicals, dissociated and/or excited atoms or molecules produced as a result of an applied electric or electromagnetic field including any accompanying radiation which might be produced. The electromagnetic field can cover a broad frequency range, and is produced by various frequency generators.

One embodiment of a plasma sterilizing apparatus having a separate plasma generator and sterilizing chamber is described in commonly assigned, U.S. Pat. No. 5,115,166, the entire contents of which are hereby incorporated by reference. In that embodiment, the plasma is generated in a rectangular waveguide. However, maintaining the process gas pressure in the generator higher than the sterilizer vacuum chamber pressure was found to be necessary to obtain and retain a stable plasma in the plasma generating chamber, and this required the presence of a restriction in the generator outlet passageway. With some gases, the use of a secondary energy source such as a spark was found to be necessary to initiate the plasma. In contrast, with the cylindrical waveguide plasma generator in the sterilizer of this invention, the plasma can be reliably initiated and maintained at suitable process gas pressures without the use of a secondary energy source.

Figure 1:
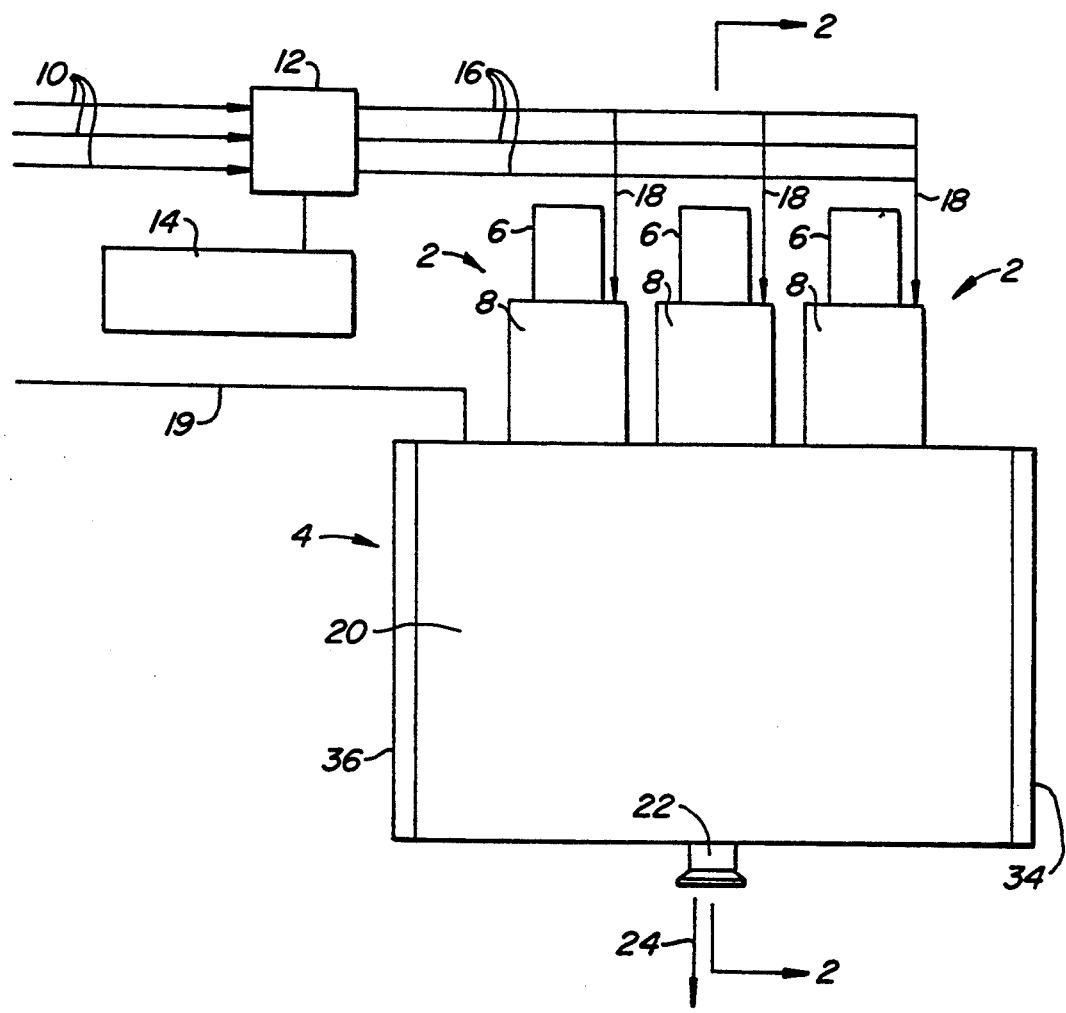
FIG. 1 is a front view of the plasma sterilizer of this invention.

FIG. 1 is a front view of the plasma sterilizer of this invention. The plasma sterilizer comprises one or more plasma generators 2 and a sterilizing cabinet 4. The plasma generators includes electromagnetic field generators 6 and cylindrical waveguides 8 which can be supported on the sterilizing cabinet 4.

The electromagnetic field generator 2 can be a microwave source such as a magnetron, a klystron, a travelling-wave tube or a gyrotron. For large installations, the electromagnetic field generator 2 can operate in the radio-frequency range. In the preferred implementation, a magnetron is used.

The plasma source gases are fed through process gas supply tubes 10 to a control valve complex 12. The operation of the control valves is controlled by standard procedures with a conventional central processing unit (CPU) 14 connected therewith. The gas flows providing the precise process gas mixture desired are thus regulated. The process gases are directed by supply tubes 16 to the plasma chamber inlet conduits 18 where they mix to form the desired process gas compositions.

Additional treatment fluids such as antimicrobial agents can be introduced directly into the sterilizing cabinet by secondary treatment fluid conduit 19. For example, the cylindrical waveguide plasma sterilizer of this invention can be used with peracetic acid and/or hydrogen peroxide treatments of the articles such as disclosed in U.S. Pat. No. 5,084,239.

The sterilizing cabinet has a door 20 and a exhaust gas outlet port 22 connected to a conventional exhaust vacuum system (not shown), through which exhaust gases 24 are removed. With a suitable selection of process gases, the exhaust gases are environmentally safe and non-toxic.

Figure 2:
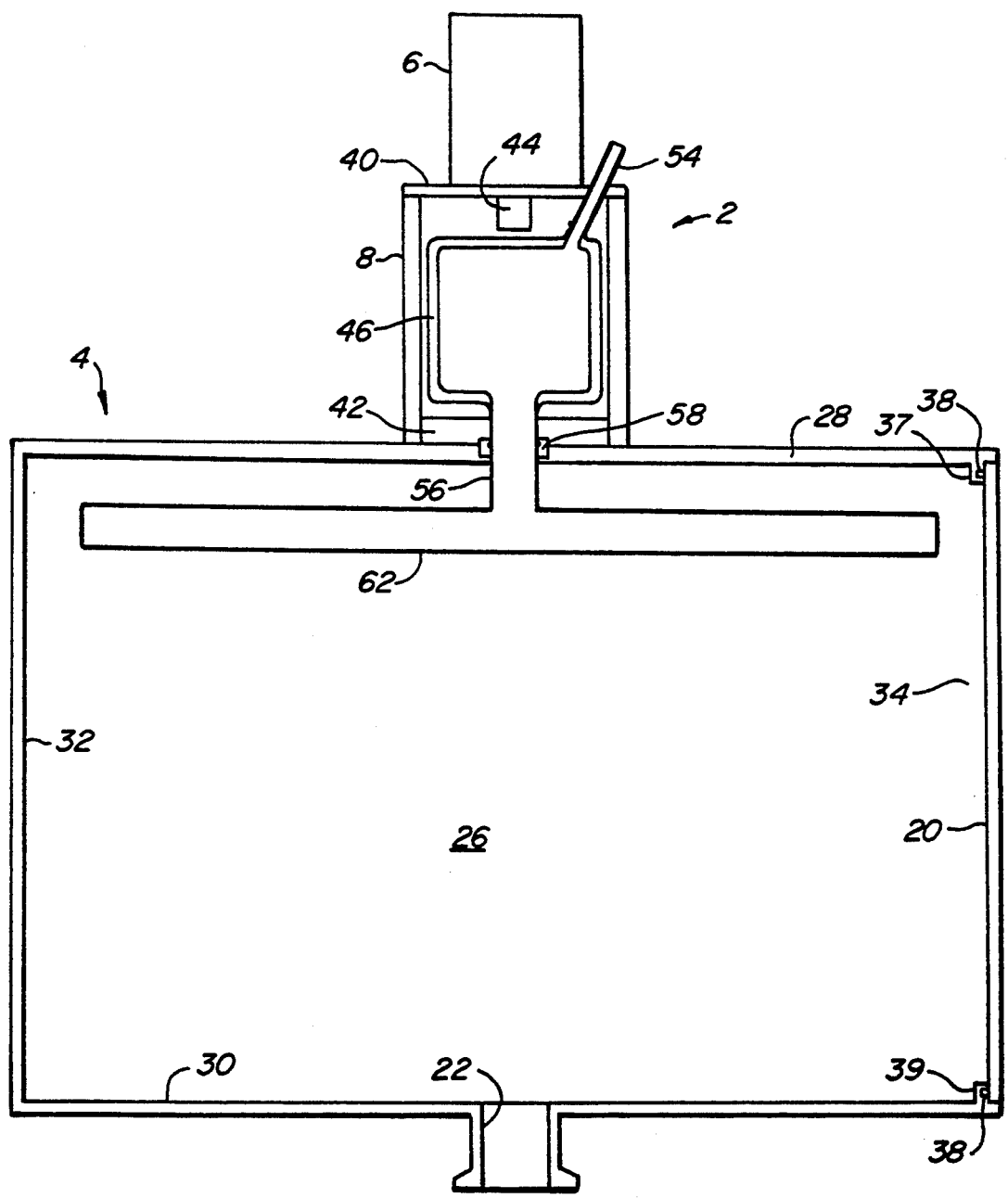
FIG. 2 is a cross-sectional view of the plasma sterilizer of FIG. 1, taken along the line 2—2 of FIG. 1.

FIG. 2 is a cross-sectional view of the plasma sterilizer of FIG. 1, taken along the line 2—2 of FIG. 1. The sterilizing cabinet 4 comprises a sterilizing chamber 26 defined by metallic ceiling and floor plates 28 and 30, backplate plate 32, door 20, and end plates 34 and 36 (FIG. 1). The door 20 is secured in a sealed relationship with the sterilizing chamber. It is hinged at the top, side or bottom with conventional hinge pins (not shown) to swing against abutting surfaces 37 and 39, and an O-ring seal 38.

Figure 3:
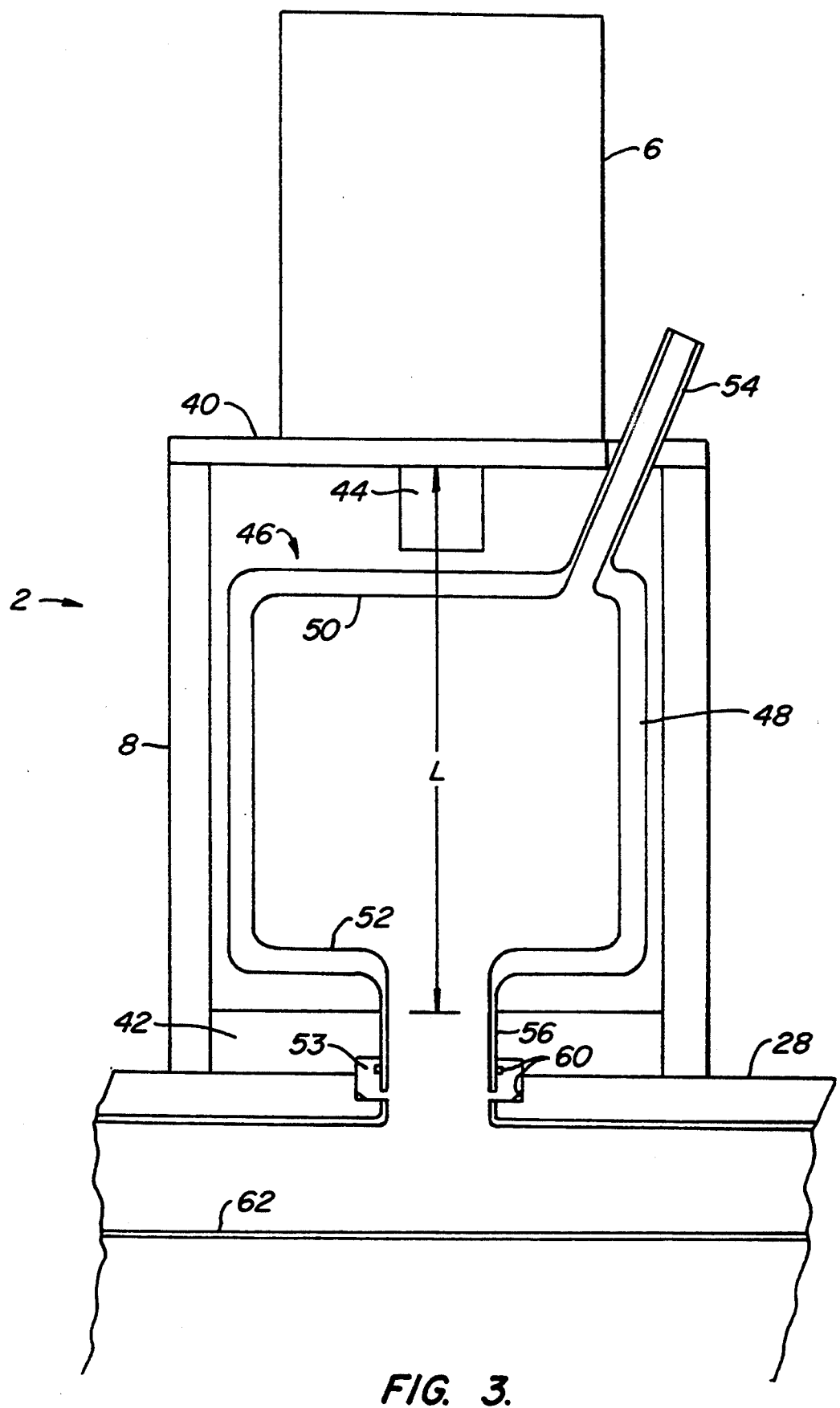
FIG. 3 is a detailed, fragmentary cross-sectional view of the cylindrical microwave plasma generator of this invention.

FIG. 3 is a detailed, fragmentary cross-sectional view of the cylindrical microwave plasma generator of this invention. The plasma generator 2 comprises the metallic cylinder 8, metallic support plate 40 for supporting the electromagnetic field generator and the antenna and metallic shorting floor plate 42. The antenna 44 is axially concentric with the cylinder 8. The plasma is generated in the cylindrical plasma container 46 made of a material which is transparent to electromagnetic radiation and has the strength to withstand reduced pressure when evacuated. A suitable material is quartz or pyrex, for example. The plasma container 46 is essentially a bottle with a cylindrical sidewall 48 and integral top and bottom ends 50 and 52. It has an integral process gas inlet conduit 54 for introducing a flow of process gases into the interior of the container where the plasma is produced. It also has an integral plasma outlet conduit 56 through which gaseous plasma products are fed to distributor 62 and into the sterilizing chamber. The plasma container outlet conduit 56 passes into the sterilizing chamber through an opening in the metallic shorting floor plate 42 and sealing ring 58. The opening does not appreciably compromise the confinement of the electromagnetic field within the shield provided by the metallic cylinder 8, the metallic support plate 40 and the metallic shorting floor plate 42. Sealing ring 58 has two O-ring seals 60 which form a seal between the outer surface of the conduit 56 and the top plate 28 of the sterilizing cabinet. The plasma outlet conduit 56 leads to plasma distributor 62 via a restriction means (not shown). The plasma distributor has holes (not shown) in the lower surface to distribute gaseous plasma products across the full width of the sterilizing cabinet. The plasma products flow downward over objects to be sterilized and are exhausted through outlet port 22.

The cylindrical waveguide plasma generator produces plasmas more efficiently with less power and lower gas consumption than rectangular waveguide configurations with RF generator systems. It allows operation independent of power and flow within a given band. The cylindrical waveguide is preferably operated in the $TM_{01}$ mode described by Rissi and Veley (supra) because of the increased energy coupling into the gas which satisfies the equation E/P as mentioned previously. In this mode, the electromagnetic field generator couples into the waveguide axially, not from the side.

Electromagnetic field frequencies within the range of from about 915 MHz to $10^6$ MHz can be easily generated by conventional electromagnetic field generator microwave generators. Preferred frequencies are within the range of from about 915 MHz to 2450 MHz because of cost, FCC regulations and waveguide sizing considerations. Electromagnetic field generators that operate at 2.45 GHz are the most practical due to their use in the commercial heating marketplace where the large volume has brought the price down.

To insure propagation of the $TM_{01}$ mode only, the upper frequency limit of the electromagnetic field generator is preferably set five percent below the cutoff frequency of the $TM_{11}$ mode. The lower frequency is preferably set to approximately twenty-five percent above the cutoff frequency of the $TM_{01}$ mode.

Figure 4A:
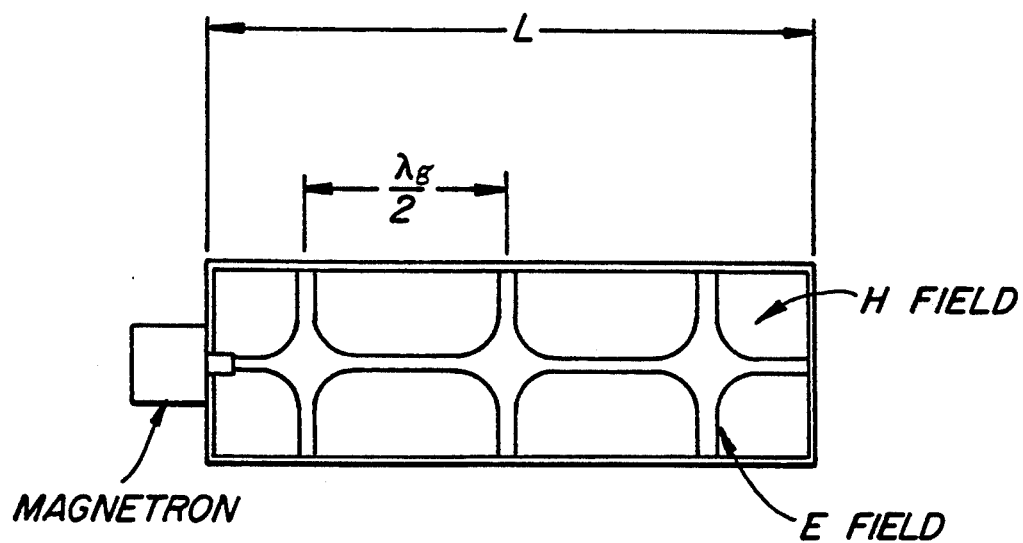
FIGS. 4A–4B are respectively detailed, cross-sectional side and end views of the electro (E) & magnetic (H) field for a $TM_{01}$ wave propagation for a circular waveguide.
Figure 4B:
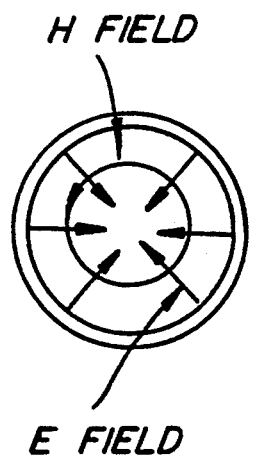

The axial length of the cylindrical waveguide, L, is the distance between the antenna support plate 40 of the antenna 44 and the shorting end plate 42. The waveguide length, L, is selected based on increments of $\lambda_g/2$ as shown in FIG. 4. Therefore, the guide wavelength ($\lambda_g$) can be determined by the formula:

$$\lambda_g = \frac{\lambda}{\sqrt{1 - \left(\frac{f_c}{f}\right)^2}}$$

wherein $\lambda_g$ is the guide wavelength of the electromagnetic field generator, which is further defined by the operating frequency of the electromagnetic field generator, i.e.

$$\lambda = 30/f$$

where:
  $\lambda$ = wavelength (cm)
  f = frequency (GHz)
  $f_c$ = cutoff frequency (GHz).

The apparatus can be used to generate a sterilizing plasma from a mixture of oxygen; argon, helium, and/or nitrogen; and hydrogen, or with a mixture of air and hydrogen, supplemented by oxygen or nitrogen to give the desired ratios. The sterilization is carried out at a vacuum pressure of from 0.01 to 100 torr and preferably from 0.1 to 15 torr. Sterilization may be carried out at higher pressures provided steps are taken to ensure uniformity of gas flows and temperature throughout the chamber. The temperature in the sterilizing chamber is maintained below 80° C. and preferably from 38° to 60° C. for articles that can not tolerate high temperatures. Elevated temperatures may preferably be used with articles capable of withstanding them.

The apparatus disclosed herein is capable of producing plasma having uncharged, highly reactive species. For example, in the plasma generating chamber, oxygen is energized by microwave radiation and forms a plasma having an initial high concentration of ions and ultraviolet emissions. These are not allowed into the sterilization chamber as they tend to be strongly destructive on the article to be sterilized, or the packaging. The UV emissions are localized in the plasma generating chamber and are attenuated by the restriction means and the plasma distribution means before they reach the sterilizing chamber. Similarly, as high energy ions hit the restriction means and the internal wall of the plasma distribution means, they recombine with free electrons to revert to uncharged, highly reactive free radicals. By the time the plasma enters the sterilizing chamber, the plasma's downstream products include high concentration of highly reactive uncharged free radicals, uncharged atoms and excited molecules.

Typically, a microwave source is used to generate the plasma. It is channeled by a waveguide to form a highly confined electromagnetic (EM) field zone. Little of that field can spread to the sterilizing chamber. Thus, production of high energy ions and UV is only possible in the field region of the plasma generating chamber and not outside of it. Also, there is no EM field to cause non-uniformity in the sterilizing chamber. The restriction means, apart from obstructing the passage of UV and ions as noted above, further helps to make plasma generation outside the plasma generating chamber less favorable. The restriction means maintains an optimal gas pressure in the plasma generating chamber for generating plasma. Once the gas exits via the restriction means, the pressure and the EM field drop to make generation impossible under normal conditions. Thus, Uv and ions can only be generated in the plasma generating chamber; once outside, they are allowed to dissipate to form a downstream plasma consisting essentially of energized, highly reactive uncharged free radicals, atoms and excited molecules.

Under these conditions, effective sterilization is effected without significant deterioration of packaging materials in which articles to be sterilized may be placed.

The method of this invention for plasma sterilization comprises exposing an article to be sterilized to a plasma generated from a gaseous mixture of argon, helium or nitrogen mixed with oxygen and/or hydrogen at temperatures of less than 60° C., a pressure of from 0.01 to 100 torr, preferably from 0.1 to 15 torr and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases. The gas mixtures producing plasmas for sterilizing packages preferably contain from 1 to 10 (v/v) % oxygen and from 2 to 8 (v/v) % hydrogen, and optimally contain from 2 to 8 (v/v) % oxygen and from 3 to 7 (v/v) % hydrogen. Packages are treated for at least 15 minutes and preferably from 1 to 5 hours.

In an alternate embodiment, packaged goods are sterilized by treatment for at least 15 minutes and preferably from 1 to 5 hours with plasma generated from a gas mixture containing from 1 to 10 (v/v) % hydrogen and from 90 to 99 (v/v) % argon, helium and/or nitrogen, with little or no amounts of oxygen being present, the optimum mixture comprising 5 (v/v) % hydrogen and about 95 (v/v) % argon.

Objects which are resistant to oxidation such as metallic surgical instruments can be sterilized by treatment for at least 1 minute and preferably for at least 5 minutes with plasma generated from a gas mixture containing from 10 to 40 (v/v) % oxygen; from 60 to 90 (v/v) % argon, helium and/or nitrogen; and optional amounts of hydrogen and/or inert gases at a pressure of from 0.01 to 100 torr, preferably from 0.1 to 15 torr. The plasma can be generated from air (21 v/v % oxygen, 78 v/v % nitrogen, etc.), for example.

It is to be understood that the operating temperature of the present process is determined by the characteristics of the articles being sterilized, not by temperature limitations of the sterilization process. Many medical articles to be sterilized will not withstand temperature over 60° C. while other articles such as metallic surgical instruments are more efficiently sterilized at higher temperatures.

Similarly, the pressure limitations given are examples illustrative of the preferred embodiments. Different pressure limits are contemplated for other plasma sterilizers having different dimensions and surface characteristics.

A processing time of from 5 to 10 minutes is usually sufficient to sterilize most articles. Clean articles packaged in envelopes or other shapes having porous surfaces allowing easy penetration of the plasma are usually completely sterilized within 60 minutes.

In an optimum method of sterilizing, the articles to be sterilized are placed in the sterilizing chamber, supported by conventional fixtures which permit the plasma gas products to reach all surfaces of the articles. The chamber is closed, the sterilizing chamber is evacuated, plasma generation is begun, and the plasma gas products are directed into and through the sterilizing chamber.

The plasma components have a short life, and quickly decay to form water vapor (gas), carbon dioxide, and other non-toxic components usually found in air. These are fully acceptable as residues or as exhaust gas components.

It is claimed:

1. An apparatus for plasma sterilization comprising:
a sterilization chamber;
a plasma container made of a material transparent to an electromagnetic radiation, said plasma container having a gas inlet for admitting a plasma generation gas and a plasma product outlet conduit for passing plasma gas products into said sterilization chamber;
at least one microwave plasma generator for producing the plasma gas products in said plasma container, said microwave plasma generator further comprising:
a electromagnetic energy source for generating electromagnetic radiation,
a cylindrical metal waveguide enclosing said plasma container for guiding the electromagnetic radiation thereto, and
an axially concentric antenna extending into the cylindrical waveguide for feeding the electromagnetic radiation from the electromagnetic energy source to the cylindrical waveguide.

2. An apparatus of claim 1 wherein the plasma container is made of quartz.

3. An apparatus of claim 1 wherein the plasma container is concentric with the waveguide.

4. An apparatus of claim 1 wherein the electromagnetic energy source is a magnetron.

5. An apparatus of claim 1 wherein the electromagnetic energy source is a klystron.

6. An apparatus of claim 1 wherein the electromagnetic energy source is a travelling-wave tube.

7. An apparatus of claim 1 wherein the electromagnetic energy source is a radio-frequency source.

* * * * *